(12) United States Patent
Deuar

(10) Patent No.: US 7,743,668 B2
(45) Date of Patent: Jun. 29, 2010

(54) METHOD AND APPARATUS OF TESTING POLES

(75) Inventor: Krzysztof Jan Deuar, Queensland (AU)

(73) Assignee: Anna Teresa Deaur, Morayfield, Queensland (AU)

( * ) Notice: Subject to any disclaimer, the term of this patent is extended or adjusted under 35 U.S.C. 154(b) by 227 days.

(21) Appl. No.: 10/592,792

(22) PCT Filed: Mar. 15, 2005

(86) PCT No.: PCT/AU2005/000359

§ 371 (c)(1),
(2), (4) Date: May 1, 2007

(87) PCT Pub. No.: WO2005/090943

PCT Pub. Date: Sep. 29, 2005

(65) Prior Publication Data

US 2007/0283765 A1   Dec. 13, 2007

(30) Foreign Application Priority Data

Mar. 16, 2004   (AU) .............................. 2004901329

(51) Int. Cl.
*G01M 3/00* (2006.01)
*G01M 5/00* (2006.01)
*G01N 11/00* (2006.01)

(52) U.S. Cl. ............................ 73/788; 73/786; 73/823; 73/849

(58) Field of Classification Search ................. 73/823, 73/849, 786, 788; 702/43
See application file for complete search history.

(56) References Cited

U.S. PATENT DOCUMENTS

| 5,051,919 | A |   | 9/1991 | Deuar |
| 5,212,654 | A | * | 5/1993 | Deuar ........................ 73/849 |
| 6,647,801 | B1 |  | 11/2003 | Deuar |

FOREIGN PATENT DOCUMENTS

EP         638794 BQ         4/1998

OTHER PUBLICATIONS

Mokwa, Robert. "Investigation of the Resistance of Pile Caps to Lateral Loading" Thesis.. Sep. 28, 1999. Accessed online Jan. 11, 2009. <http://web.archive.org/web/20010725195420/http://scholar.lib.vt.edu/theses/available/etd-093099-180817/>.*

* cited by examiner

*Primary Examiner*—Lisa M Caputo
*Assistant Examiner*—Jonathan Dunlap
(74) *Attorney, Agent, or Firm*—Hoffman, Wasson & Gitler, P.C.

(57) ABSTRACT

A method for testing poles (1) including the steps of applying a first load to a pole (1), measuring the movement of the pole (1), at least partially de-loading the pole (1) to a second load, measuring the movement of the pole (1), and using the change in the movement measurements under the respective loads to calculate the pole (1) stiffness.

8 Claims, 2 Drawing Sheets

METHOD AND APPARATUS OF TESTING POLES

FIELD OF THE INVENTION

The present invention relates to a method and apparatus for the testing of poles and particularly to a method and apparatus for testing poles to calculate a theoretical maximum strength of a pole. Throughout the specification, the term "poles" shall be used to include electricity, telephone and telegraphic poles; fence and retaining wall posts and the like.

BACKGROUND ART

Power poles and telephone poles are conventionally formed from wood, steel or concrete and are pounded into the ground, or a hole is drilled into the ground and the pole is inserted into the hole.

Once the pole has been put into the ground, the upper part of the pole is arranged to receive power cables, data cables, telephone cables and the like. For some poles, the weight of these cables can be quite considerable and some poles contain additional devices such as power transformers which are quite heavy.

Wood rot, bores, termites and other factors operate to reduce the strength, and therefore, the service life of poles. For safety reasons, the strength of the poles must be periodically checked and the future life of the poles established. As wood rot generally occurs below the ground level, a simple visual inspection is not sufficient and mechanical strength tests must be carried out.

To date, no simple, efficient and reliable test method has been available so poles are often replaced well before the end of their effective life.

This naturally increases the operating expenses of the electricity authority.

A known method to test the strength of a pole is to apply a load to the pole. This is usually done using a hydraulic ram which pushes or pulls the pole. However, applying a pushing force or a pulling force directly to the pole using a ram or similar device has some disadvantages. Therefore, there would be an advantage if an improved method and apparatus could be provided to test a pole.

The inventor of the present invention has been particularly active in the past in devising methods and apparatus to test the strength of poles in order to determine fitness for the purpose to which they are put.

One of the methods for testing the pole strength uses a means to calculate the minimum required strength of the pole and load to be applied to the pole equivalent to the minimum strength, a means to apply a load to the pole, means to measure the load applied to the pole, and (a) means to calculate the residual strength of the pole from the applied load, or (b) means to measure the displacement of the pole under the applied load, means to calculate the residual strength of the pole from the applied load and the displacement, and means to detect the pole failure.

The prior art methods and apparatus test whether the pole possessed a predetermined minimum strength by simulating a maximum load for the predetermined strength. This generally produced a "yes/no" answer to the question whether the pole possessed the minimum strength or not. Generally, the prior art simulation applied a load that was equal to the maximum anticipated wind load on the pole multiplied by an appropriate safety factor.

During the course of developing and using the above method, the inventor discovered that the method and apparatus that was in use had drawbacks. The prior system required the establishment and use during the testing of a reference in order to measure the flexion or displacement of the pole. This reference became difficult to establish in difficult terrain, particularly when the ground is undulating or hilly.

Further, the method used was found to contain certain inaccuracies which could be improved upon. The inventor theorized that these inaccuracies may stem from the application of a load to the pole and the subsequent movement of the pole.

It will be clearly understood that, if a prior art publication is referred to herein, this reference does not constitute an admission that the publication forms part of the common general knowledge in the art in Australia or in any other country.

SUMMARY OF THE INVENTION

The present invention is directed to a method and apparatus for testing poles, which may at least partially overcome at least one of the abovementioned disadvantages or provide the consumer with a useful or commercial choice.

In one form, the invention resides in a method for testing poles including the steps of:
  a. Applying a first load to a pole;
  b. measuring the movement of the pole;
  c. at least partially de-loading the pole to a second load;
  d. measuring the movement of the pole;
  e. using the change in the movement measurements under the respective loads to calculate the pole stiffness.

The inventor has found that when using his previous pole testing apparatus and method to test in-ground poles, applying a load to the pole caused movement having at least two different components, namely:
  a. rotation of the lower portion of the pole below the ground surface (rotation movement); and
  b. movement of the pole induced by the applied load (true or material movement).

The degree of movement or pole tilt is preferably used in the testing of the strength of poles. Whilst not wishing to be limited by theory, the inventor postulates that the rotation of the lower portion of the pole below the ground surface as a result of the applied load, is a source of error when measuring the degree of movement of the pole, as tilting of the pole in the ground can lead to a systematic bias error in the measurement of movement. The bias of the measurement of the movement of the pole will generally be upward due to the pole being tilted as well as undergoing movement. The present invention may overcome this bias by measuring the pole movement under a first load to force the pole to rotate in the ground, measuring the movement under this load, partially de-loading the pole and taking a second measurement of movement.

The inventor maintains that when the first load is applied, the pole is forced to undergo rotation in the ground. By measuring the movement under the first load, at least partially de-loading and then taking a second measurement of movement, the component of movement due to pole rotation as opposed to actual true movement can be accounted for. This rotation movement can be calculated and then removed from the total movement measurement. Alternatively, by zeroing the movement measurement apparatus whilst under the first load, the rotation movement measurement can be removed from the movement measurement altogether. The second measurement may therefore be a total movement measurement including an amount for rotation movement or a corrected amount corresponding to true movement only.

Preferably, the pole may be only partially de-loaded during the de-loading step. Again, not wishing to be limited by theory, the inventor theorizes that soils undergo a plastic deformation whilst loaded to the first load. Partial de-loading but maintaining a smaller load on the pole may allow the pole to be maintained in position in the plastically deformed soil and thereby reduce the error due to rotation movement.

Steps (c) and (d) of the above method may typically be repeated more than once. There may for example be multiple de-loading steps in order to establish a series of movement measurements of a pole under different applied loads.

The method may further comprise the step of using the calculated pole stiffness to calculate the theoretical maximum strength of the pole. The calculation of theoretical maximum strength using the pole stiffness may require the calculation or use of mechanical properties of the materials of construction for the pole being tested.

The de-loading step only partially de-loads the pole but maintains a load on the pole to prevent pole rotation in the ground. Generally, the first load applied to the pole may be a target or pre-load. The pre-load limit may be calculated to simulate an operating load which may included such factors as wind shear and the forces imposed on poles by the attachment and support of wires at an upper portion of the pole. These wires impose tension or compression forces at the upper portion of the pole.

Preferably, during the de-loading step may lessen the first load to no less than approximately 20% of the first load. The actual de-loading factor or amount may typically be dependant upon the soil type as soil type will affect the amount of plastic deformation and thus the rotational movement amount.

The load applied to the pole will typically also be measured and recorded in order for use in calculations. Any method and apparatus for measuring load can be used to achieve this.

In a second form, the invention may reside in an apparatus for testing poles including means to apply a load to a pole, means to measure the load applied to the pole, at least one means to measure the movement of the pole under an applied load, and means to calculate at least the stiffness of the pole from the movement of the pole under at least two different applied loads.

In a more particular form, the invention may reside in an apparatus for testing poles including means to apply a load to a pole, means to measure the load applied to the pole, at least one means to measure the movement of the pole under an applied load, at least one measurement being taken under loaded conditions and at least one measurement being taken under at lest partially de-loaded conditions and means to calculate at least the stiffness of the pole from the movement of the pole under at least two different applied loads.

There may be one or more than one means to measure movement. The means to measure movement of the pole may preferably by displacement gauges, strain gauges, digital protractors or the like.

More than one measurement apparatus may be used to give a more complete representation of the loads and/or forces acting on a pole. For example, by providing a pair of measurement devices, one below and one above the loading point of the pole and establishing the difference (if any) between the readings of the pair in response to a particular load may allow the calculation of the force acting on an upper portion of the pole by wires or other applied forces. For example, when wires are attached or suspended from an upper portion of the pole, the measurement of the device located below the loading point may give an indication of true movement of the pole due to the load imposed by the loading apparatus and the measurement of the device located above the loading point may give an indication of force applied at the upper portion of the pole by the tension of the wires.

Preferably the means to measure movement measure the degree of tilt of the pole from the vertical. Alternatively, the measurement may be the degree of tilt from a reference angle which may be established as a part of the test. Preferably, the measurement of pole tilt may be taken from a zeroing of the measurement apparatus upon application of the first load.

The load may be applied by pushing and/or pulling the pole at any height above or below the ground level and may be affected by a mechanical jack or turnbuckle, hydraulic or pneumatic ram, a winch or other suitable mechanical, hydraulic or electrical means which may be portable, mounted on wheels or vehicles.

The applied load is preferably measured by a load cell or other suitable equivalent means.

The applied loads and other test data as well as pole test results may be recorded manually or automatically by the use of any suitable computer system.

Stability of the pole in case of its failure can be provided by a safety frame or safety rope or pole buoy or safety clamps mounted to the boom of the crane of the pole testing vehicle or other heavy equipment.

Excessive movement of the pole during the application and/or removal of load applied thereto may be limited by a chain, rope, frame, pole buoy, bar, or clamps connected to the pole testing equipment or other heavy and stable machinery and objects such as concrete blocks, adjacent trees or the like.

BRIEF DESCRIPTION OF THE DRAWINGS

Various embodiments of the invention will be described with reference to the following drawings, in which.

DETAILED DESCRIPTION OF THE PREFERRED EMBODIMENT

According to a preferred embodiment of the present invention, a method and apparatus for testing poles is provided.

Figure 1:
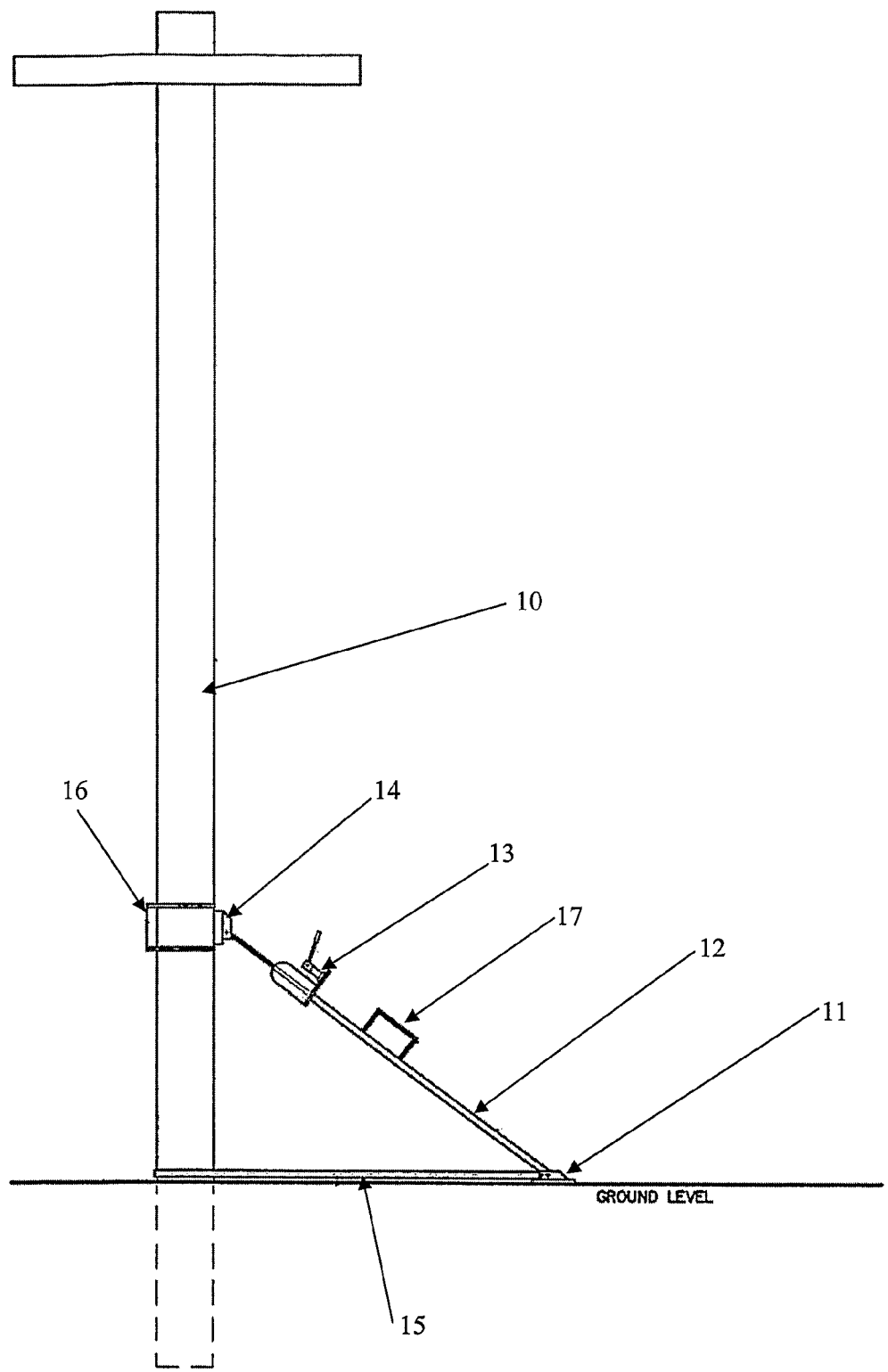
FIG. 1 is a schematic side view of an apparatus according to a preferred embodiment of the present invention.

The method of the preferred embodiment is implemented using an apparatus for testing poles as illustrated in FIG. 1, including means to apply a load to a pole 10. The means to apply the load to the pole includes a ground bearing foot member 11, a strut 12 extending generally upwardly from the foot member 11 and a hydraulic ram 13 to adjust the length of the strut 12. By extending or retracting the strut 12, differing loads can be applied to the pole 10. At the opposite end of the strut 12 from the foot member 11, there is a pole engagement member 14. The load is applied by pushing the pole at any height above the ground level and is affected by a mechanical jack or turnbuckle, hydraulic or pneumatic ram, a winch or other suitable mechanical, hydraulic or electrical means which is portable.

The foot member 11 is also equipped with a restraining strap 15, chain or belt. This applies pressure to the pole 10 and helps prevent the foot member 11 from moving when the load is applied to the pole. The strut is also equipped with a handle 17.

The hydraulic ram has an associated means (not illustrated) to measure the load applied to the pole 10. The applied load is measured by a load cell or other suitable equivalent means.

The apparatus further includes at least one means to measure the movement of the pole under an applied load. These means are generally displacement gauges, strain gauges, digital protractors 16 or the like.

Figure 2:
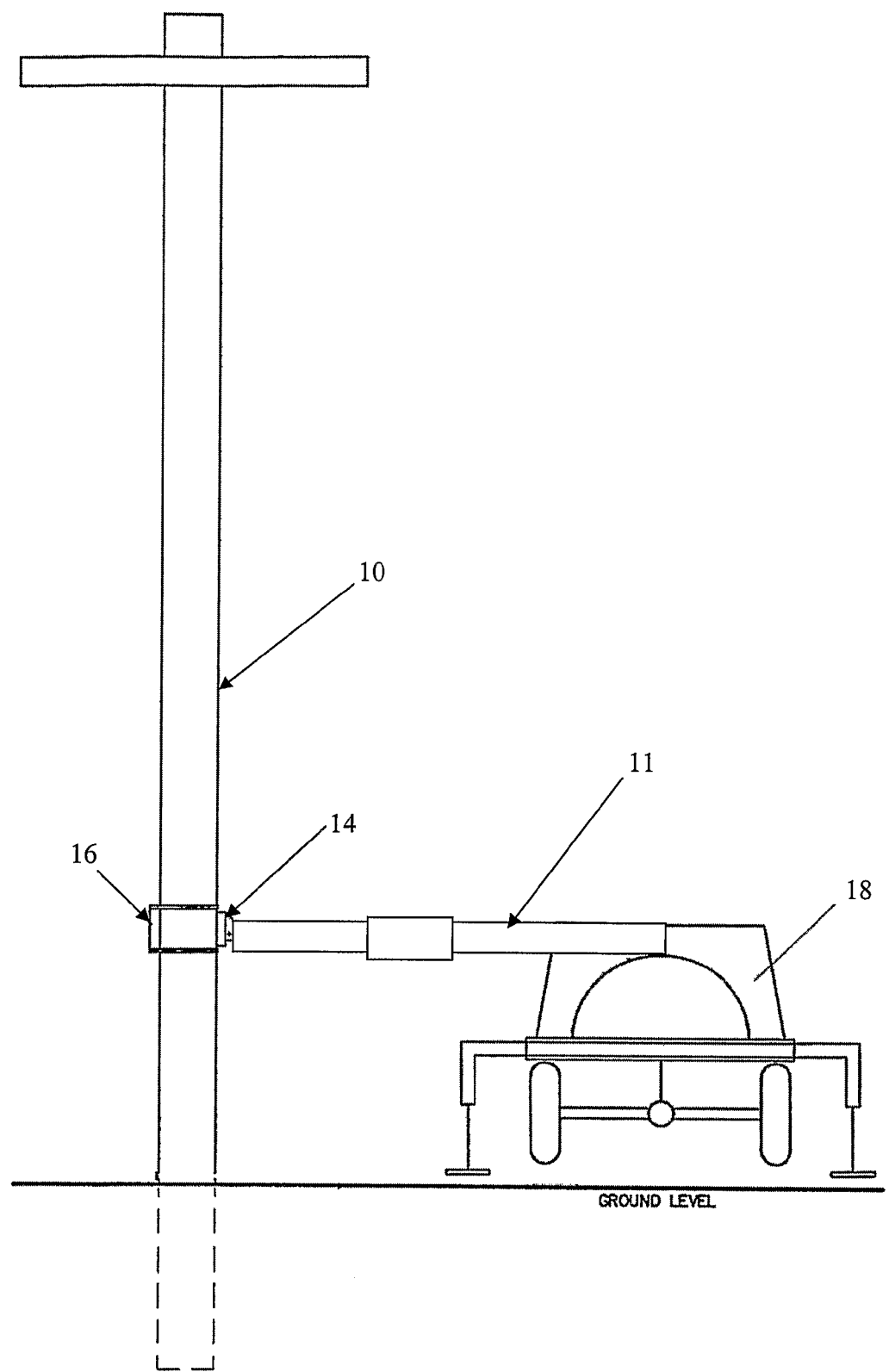
FIG. 2 is a schematic side view of an apparatus according to an alternative preferred embodiment of the present invention.

According to the embodiments illustrated in FIGS. 1 and 2 only one digital protractor is used. The digital protractor measures the degree of tilt of the pole from the vertical or from a reference angle which is established as a part of the test.

However, more than one digital protractor 16 can be used to give a more complete representation of the loads and/or forces acting on a pole. For example, by providing a pair of measurement devices 16, one below and one above the loading point of the pole 10 and establishing the difference (if any) between the readings of the pair in response to a particular load may allow the calculation of the force acting on an upper portion of the pole 10 by wires or other applied forces. For example, when wires are attached or suspended from an upper portion of the pole 10, the measurement of the device 16 located below the loading point may give an indication of true movement of the pole 10 due to the load imposed by the loading apparatus and the measurement of the device 16 located above the loading point may give an indication of force applied at the upper portion of the pole by the tension of the wires.

The embodiment of the invention illustrated in FIG. 2 is similar in principle to that of FIG. 1 but instead of the means to apply a load to a pole being provided with a foot 11, the strut 12 is provided on a movable vehicle 18.

The method for testing poles 10 includes the steps of
a. applying a first load to a pole 10;
b. measuring the movement of the pole 10;
c. at least partially de-loading the pole 10 to a second load;
d. measuring the movement of the pole 10;
e. using the change in the movement measurements under the respective loads to calculate the pole stiffness.

The inventor has found that applying a load to a pole 10 caused movement having at least two different components, namely:
a. rotation of the lower portion of the pole 10 below the ground surface (rotation movement); and
b. movement of the pole 10 induced by the applied load (true or material movement).

The present invention may overcome the bias or error dure to rotation movement by measuring the pole movement under a first load to force the pole to rotate in the ground, measuring the movement under this load, partially de-loading the pole and taking a second measurement of movement.

When the first load is applied which is generally a fraction of the required pole strength, the pole is forced to undergo rotation in the ground. By measuring the movement or bending under the first load, at least partially de-loading and then taking a second measurement of movement or bending, the component of movement due to pole rotation as opposed to actual true movement can be accounted for. By zeroing the movement measurement apparatus whilst under the first load, the rotation movement measurement can be removed from the movement measurement altogether. The second measurement will therefore be a total movement measurement including an amount for rotation movement or a corrected amount corresponding to true movement only.

The pole is only partially de-loaded during the de-loading step to account for the plastic deformation of the soil around the base of the pole whilst loaded to the first load. Partial de-loading but maintaining a smaller load on the pole allows the pole to be maintained in position in the plastically deformed soil and thereby reduce the error due to rotation movement.

The first load applied to the pole is a target or pre-loading force. The pre-load limit is calculated to simulate an operating load which may included such factors as wind shear and the forces imposed on poles by the attachment and support of wires at an upper portion of the pole. These wires impose tension or compression forces at the upper portion of the pole.

During the de-loading step the first load is reduced to no less than approximately 20% of the first load. The actual de-loading factor or amount is dependant upon the soil type as soil type will affect the amount of plastic deformation and thus the rotational movement amount.

The method then allows the use of the calculated stiffness to calculate the theoretical maximum strength of the pole through the application of mathematical formulae. This in turn allows a calculation of the poles serviceable life.

In the present specification, the term "movement" may preferably include any one or more of deflection, tilt, slope, inclination, attitude or rotation or other type of movement.

In the present specification and claims, the word "comprising" and its derivatives including "comprises" and "comprise" include each of the stated integers but does not exclude the inclusion of one or more further integers.

Reference throughout this specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout this specification are not necessarily all referring to the same embodiment. Furthermore, the particular features, structures, or characteristics may be combined in any suitable manner in one or more combinations.

What is claimed is:

1. A method for testing above-ground poles including the steps of
a. applying a first load to an above-ground pole,
b. measuring the movement of the pole under the first load,
c. at least partially de-loading the pole to a second load,
d. measuring the movement of the pole under the second load, and
e. using the change in the movement measurements from the first load and the second load to calculate the pole stiffness.

2. The method according to claim 1 wherein the pole is only partially de-loaded during the de-loading step.

3. The method according to claim 1 wherein steps (c) and (d) are repeated more than once in order to establish a series of movement measurements of a pole under different applied loads.

4. The method according to claim 1 further comprising the step of using the calculated pole stiffness to calculate the theoretical maximum strength of the pole.

5. The method according to claim 1 wherein during the de-loading step, the load is decreased from the first load to no less than approximately 20% of the first load.

6. The method according to claim 1 wherein the movement measured is the pole tilt angle.

7. A method for testing above-ground poles including the steps of
a. applying a first load to an above-ground pole,
b. measuring the movement of the pole under the first load,
c. at least partially de-loading the pole to a second load,
d. measuring the movement of the pole under the second load, and e. using the change in the movement measurements from the first load and the second load to calculate the pole stiffness, wherein the second load is calculated dependent upon the soil type.

8. A method for testing above-ground poles including the steps of a. applying a first load to an above-ground pole, b. measuring the movement of the pole under the first load, c. at least partially de-loading the pole to a second load, d. measuring the movement of the pole under the second load, and e. using the change in the movement measurements from the first load and the second load to calculate the pole stiffness, wherein the measurement step b. following application of the first load is a zeroing measurement.

* * * * *